United States Patent
Stahl et al.

(10) Patent No.: US 6,216,035 B1
(45) Date of Patent: Apr. 10, 2001

(54) DETERMINATION OF PACEMAKER WENCKEBACH AND ADJUSTMENT OF UPPER RATE LIMIT

(75) Inventors: Wyatt K. Stahl, Vadnais Heights; John M. Voegele, East Bethel, both of MN (US); Rick P. Conville, Columbia, MD (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/412,673

(22) Filed: Oct. 5, 1999

(51) Int. Cl.[7] ..................................................... A61N 1/362
(52) U.S. Cl. ................................................. 607/9; 607/14
(58) Field of Search ............................................. 607/9, 14

(56) References Cited

U.S. PATENT DOCUMENTS

| | | |
|---|---|---|
| 4,712,556 | 12/1987 | Baker, Jr. . |
| 5,144,949 | 9/1992 | Olson . |
| 5,193,550 | 3/1993 | Duffin . |
| 5,247,929 | 9/1993 | Stoop et al. . |
| 5,282,465 | 2/1994 | van der Veen et al. . |
| 5,395,397 | 3/1995 | Lindgren et al. . |
| 5,423,868 | 6/1995 | Nappholz et al. . |
| 5,441,523 | 8/1995 | Nappholz . |
| 5,496,350 | * 3/1996 | Lu ........................................... 607/14 |
| 5,522,858 | 6/1996 | van der Veen . |
| 5,531,771 | 7/1996 | van der Veen . |
| 5,549,648 | 8/1996 | Stoop . |
| 5,609,610 | 3/1997 | Nappholz . |
| 5,609,613 | 3/1997 | Woodson et al. . |
| 5,622,178 | 4/1997 | Gilham . |
| 5,674,255 | 10/1997 | Walmsley et al. . |
| 5,741,309 | 4/1998 | Maarse . |
| 5,792,183 | 8/1998 | Esler . |
| 5,794,623 | 8/1998 | Forbes . |
| 5,810,739 | 9/1998 | Bornzin et al. . |
| 5,861,007 | 1/1999 | Hess et al. . |
| 5,891,178 | 4/1999 | Mann et al. . |
| 5,893,882 | 4/1999 | Peterson et al. . |

* cited by examiner

*Primary Examiner*—George Evanisko
(74) *Attorney, Agent, or Firm*—Nikolai, Mersereau & Dietz, P.A.

(57) ABSTRACT

A dual chamber pacemaker incorporating a system for distinguishing Wenckebach episodes from pacemaker mediated tachycardia episodes based on variations in VA intervals is disclosed which provides for adjusting the MTR upward in response to a threshold frequency of incidences of Wenckebach.

20 Claims, 3 Drawing Sheets

DETERMINATION OF PACEMAKER WENCKEBACH AND ADJUSTMENT OF UPPER RATE LIMIT

BACKGROUND OF THE INVENTION

I. Field of the Invention

The present invention relates generally to the field of cardiac rhythm management and more particularly to a dual chamber cardiac pacemaker incorporating a system for discriminating between pacemaker mediated tachycardia (PMT) and simple upper rate limit Wenckebach behavior due to normal sinus tachycardia. The system may also provide for adjusting the upper rate limit (URL) or maximum tracking rate (MTR) according to the frequency of detected pacemaker Wenckebach events.

II. Related Art

In dual chamber pacemakers, circuitry is provided for both sensing atrial and ventricular depolarization events and for pacing one or both of atrial and ventricular tissue. In a subject with normal sinus node activity and interrupted conduction system, the pacemaker is able to sense an atrial depolarization (P-wave) and thereafter stimulate the ventricle in accordance with an established AV delay interval. This effectively mimics the heart's PR interval. The situation is complicated, however, by the possible occasional occurrence of an interfering retrograde conducted P-wave, possibly the result of a ventricular stimulating pulse, but one which is also sensed by the atrial sensing circuitry. Because the atrial sensing circuitry of the pacemaker cannot tell whether a sensed signal is a normal or retrograde conducted P-wave it will initiate another ventricular stimulation event. This may quickly lead to PMT. To overcome this problem, dual chamber pacemakers are typically programmed to include a post-ventricular atrial refractory period (PVARP) during which atrial events are sensed but ignored. In this manner, if an atrial event occurs during PVARP due to retrograde conduction, an AV interval is not initiated and no ventricular stimulating pulse is generated as a result of the atrial event.

The addition of PVARP does not totally successfully resolve the problem either, however, because in many pacemaker treated patients the condition of the patient is such that the retrograde conduction time varies or fluctuates depending upon physiologic feedback mechanisms. This means that a fixed, programmable PVARP may become relatively too short over time if retrograde conduction time increases and may no longer serve to inhibit PMT. Conversely, if the PVARP is programmed to be too long, this shortens the sensing window and as the pacing rate reaches the maximum atrial tracking rate or MTR set for the pacemaker, some of the desirable P-waves will fall inside the PVARP and be ignored and this will result in an undesirable drop in the ventricular pacing rate. This is known as a two-to-one block. Thus, each time a P-wave falls within PVARP and an AV block occurs for that cardiac cycle it results in a missing cardiac cycle which is undesirable because it causes short-term loss of AV synchrony and the subsequent loss of cardiac output.

Pacemaker Wenckebach is another type of undesirable upper rate limit behavior which negatively affects the patient. In pacemaker Wenckebach, as the atrial rate increases, the AV interval is lengthened so that the ventricular pacing interval does not exceed the MTR. As the atrial rate increases, a P-wave will eventually fall within PVARP and AV block will occur for that cardiac cycle. The successive lengthening of the AV interval leading to a missing cardiac cycle likewise causes short-term loss of AV synchrony and subsequent loss of cardiac output. The detection of pacemaker Wenckebach is important as an indication of a possible need for URL/MTR adjustment.

Pacemakers are implanted to typically operate within a particular beat rate or heart rate (HR) range including a particular URL or MTR which is typically picked on the conservative side by the physician who may have a minimum familiarity with the level of activity reached by the patient. The actual proper HR range for the patient may well extend above that initially programmed. This being the case, the pacer may repeatedly reach the URL or MTR because of naturally occurring sinus rhythms and pacemaker Wenckebach may then occur. (As used herein, the term Wenckebach, unless otherwise stated, refers to a pacemaker Wenckebach epidsode). Because URL or MTR may also be reached due to PMT, and PMT should be stopped as soon as possible, because of the alternate loss of cardiac output, there is a definite need to distinguish between these two phenomena.

Pacemakers have been programmed with a function to determine whether a patient is in a pacemaker mediated tachycardia (PMT) by counting intervals that are atrially sensed and ventricularly paced at the URL. After a prescribed number of successive intervals are perceived to be at the maximum rate, perhaps 16, the pacemaker assumes the existence of PMT and is programmed to extend the next PVARP a sufficient time to break or interrupt the PMT. This PVARP extension is typically about 400–500 ms. An example of this approach is found in Walmsley et al (U.S. Pat. No. 5,674,255) assigned to the same Assignee as the present invention. The contents of that patent are deemed incorporated by reference herein for any purpose. While this solution has been successful in interupting and correcting actual PMT, it is unable to predictably discriminate between URL events which are caused by PMT and which occur simply because the patient exercised to the MTR/URL.

Thus, while the above determination and aleviation of PMT has been quite successful, a need remains for adding a technique which would produce a better and more sophisticated analysis of the nature of the cause of the upper rate limit behavior. In this manner, if one could reliably determine whether the rhythm is a PMT or a Wenckebach episode due to normal sinus tachycardia, after a given number of Wenckebach events within a prescribed time, the URL or MTR could be adjusted upward so that the pacemaker range would self-adjust to be more in line with the actual activity level of the patient.

Further, in describing the related art and features of the present invention, it is believed that it would be helpful to define certain terminology. Accordingly, several definitions are presented.

Maximum Tracking Rate (MTR) or Upper Rate Limit (URL) is the maximum rate at which the paced ventricular rate will track sensed atrial events. It is applicable to the atrial synchronous pacing modes, DDD, DDDR, VVDR and VDD and is programmable quantity typically residing in the range of from about 50 to 185 pulses per minute.

AV Delay (AV) is the programmable time period from the occurrence of an atrial event, either sensed or paced, to a paced ventricular event. It is a programmable quantity typically ranging between 10 and 300 milliseconds and is active in DDD, DDI, DVI, DOO, VDD and the similar rate responsive modes.

Post Ventricular Atrial Refractory Period (PVARP) is defined as the time period after a ventricular event, either paced or sensed, during which activity in the atrium does not inhibit an atrial stimulation pulse nor trigger a ventricular stimulating pulse. It is designed to avoid atrial sensing of retrograde activity initiated in the ventricle.

VA Interval is defined as the time period from the occurrence of a ventricular event, either paced or sensed, to the occurrence of an atrial event, either sensed or paced.

Pacemaker Mediated Tachycardia (PMT). In DDD(R) and VDD(R) pacing modes, the pacemaker may detect retrograde conduction in the atrium, causing triggered ventricular pacing rates as high as the MTR. This is referred to in the literature as pacemaker-mediated tachycardia or endless loop tachycardia.

Total Atrial Refractory Period (TARP) is defined as the sum of the AV delay and PVARP.

SUMMARY OF THE INVENTION

The present invention includes a system and method for dealing with periodic patterns of tachycardia by more accurately determining the origin of the upper rate limit (URL) behavior. The system discriminates between PMT and normal sinus tachycardia and includes the capacity to adjust the URL/MTR upward by increments, possibly one, five or ten or even up to thirty beats per minute in response to a predetermined frequency of Wenckebach events, based on as few as possibly three or more events per month up to ten or more events per week.

If events are determined to be PMT, the system also may act to break episodes of PMT by increasing the PVARP interval to a predetermined longer time, say 400–500 ms, a value that insures that retrograde P-waves are not tracked for at least one beat.

As an alternative in accordance with the present invention, the PVARP may be extended by a value equal to the measured retrograde conduction time plus some constant time, particularly between about 5 ms and 100 ms, such as 50 ms. This method minimizes the PVARP extension necessary to terminate the PMT.

Pacemakers of the class in which the invention is generally applicable include a pacer control algorithm designed to determine whether a tachycardia event is a PMT or a Wenckebach event. According to the invention, a VA stability check is added to a monitoring system that counts a predetermined number of intervals, generally 16, that have been atrially sensed and ventricularly paced at the preset URL or MTR of the pacemaker and which are normally utilized to determine PMT. In accordance with the VA stability check of the invention, it has been determined that if the VA interval varies by more than a minimum amount, typically in the range of 5–50 ms, during a series of monitored beats at URL or MTR, then the event is more likely to have been caused by a Wenckebach function than by PMT. This particularly may be the case if successive shortenings of the interval are noticed during the onset of tachycardia. The retrograde conduction time generally lengthens as the beat rate increases with increased exercise and shortens with decreased activity. It has been found that if the VA interval varies by more than about 10–15%, or about 30 ms from beat to beat; the rate change is almost always found to be charcteristic of a Wenckebach event. However, even change in the range from about 5 ms to 50 ms may well be due to a natural increase in the patient's intrinsic atrial rate and changes above about 20 ms have a higher probability of being due to pacemaker Wenckebach. Thus, a deviation range from about 5 ms to 50 ms has a reasonably chance of being due to natural increases in the patient's intrinsic atrial rate; while changes from about 20 ms to 50 ms have a high probability and at 30 ms or more, the deviation is almost certain to be due to natural increases in atrial rate. this value has been selected as a non-limiting example in the detailed description below.

One successful detection system uses 32 ms as the threshold beat-to-beat VA change. This value represents about 10–15% of a typical VA interval.

If a number of naturally induced or Wenckebach events occur within a given time period, say 10 per week, or even 3 per month, this may well be indicative that a condition exists in which the URL/MTR is set too low and should be incremented by one, five or 10 or more beats per minute to better represent the actual required pacing rate range of the heart of the patient. The control program of the pacer according to the present invention may also contain the ability to adjust the URL/MTR upward from one to about 30 RPM automatically in response to the situation.

OBJECTS

Accordingly, it is a primary object of the present invention to provide a technique that more accurately distinguishes between upper rate limit behavior precipitated by a PMT and a pacemaker Wenckebach event.

It is a further object of the present invention to provide a pacemaker Wenckebach counter which indicates a cumulative number of Wenckebach events in a given time which may be used to indicate that the pacemaker is programmed at too low a URL or MTR.

A still further object of the present invention is to utilize such a Wenckebach counter as an input to a system that operates to automatically alter the pacing limit to increase the URL/MTR by a certain number of beats per minute.

These and other objects, as well as these and other features and advantages of the present invention, will become readily apparent to those skilled in the art from a review of the following detailed description of the illustrated embodiment in conjunction with the accompanying drawings in which like numerals in the several views refer to corresponding parts.

DETAILED DESCRIPTION

Figure 1:
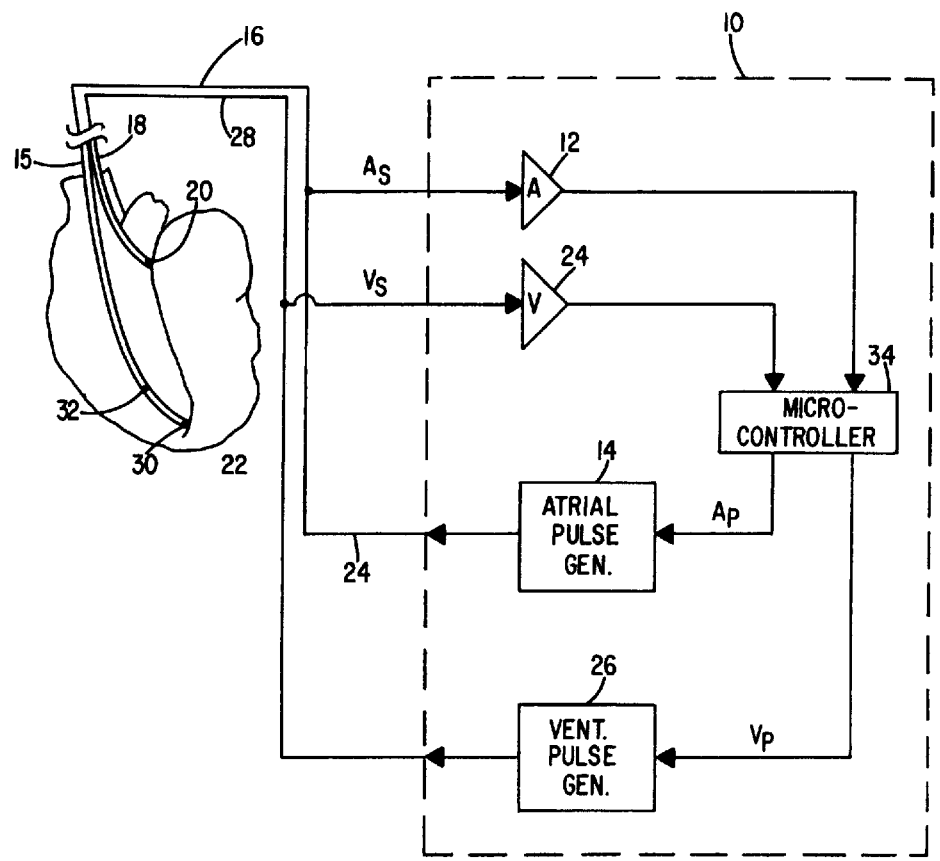
FIG. 1 is a general block diagram of a dual chamber pacemaker coupled to a heart by a pacemaker lead.

FIG. 1 depicts the operative components of an implantable dual chamber pacemaker of a class typically used for bradycardia enclosed by the broken line box 10. The pacer system includes an actual sense amplifier 12 and associated atrial pulse generator 14 which are connected by wire 16 contained in a pacing lead 18 to a sensing and pacing electrode at 20 located in the right atrium of heart represented by 22. The system also includes a ventricular sense amplifier 24 and ventricular pulse generator 26 that are connected by a conductor 28 also contained in the pacing lead 18 to an associated sensing and pacing electrode 30 disposed in the right ventricle of the heart 22. It will further be recognized that while the foregoing description pertains to a unipolar lead system, either or both leads can be bipolar, hence a second electrode 32 is illustrated on the ventricular lead 15.

The outputs from the atrial sense amplifier 12 and the ventricular sense amplifier 24 are applied as inputs to a microprocessor-based microcontroller 34 which functions to control the time of application of atrial stimulating pulses ($A_p$) and ventricular stimulating pulses ($V_p$) to the heart in a coordinated fashion determined by the software executed by the microprocessor portion of the microcontroller 34.

Figure 2:
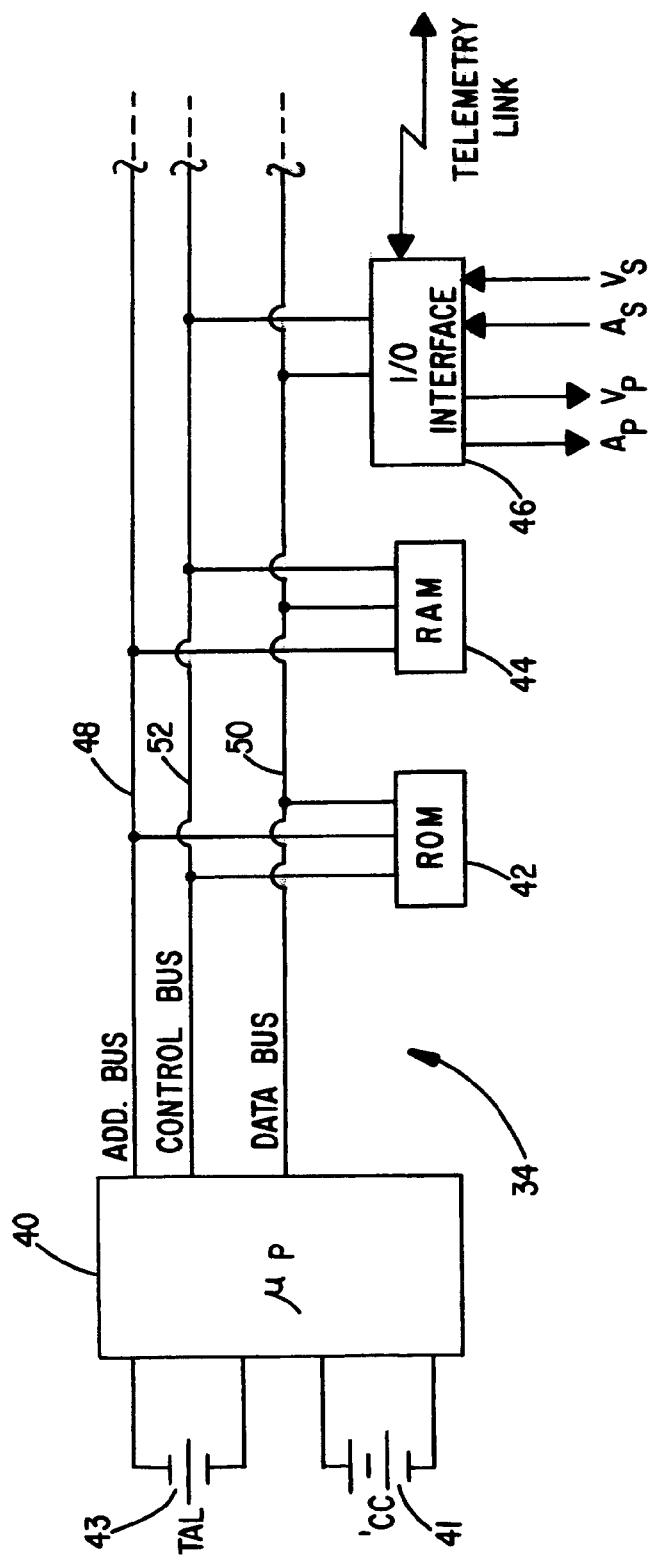
FIG. 2 is a block diagram of the microcontroller in the pacemaker of FIG. 1.

The microcontroller 34 is depicted in greater detail in the block diagram of FIG. 2 and includes a programmable microprocessor 40 formed as an integrated circuit that can be encapsulated along with a battery power supply 41 within a hermetically sealed can as is well known in the art. The microprocessor 40 includes a clock oscillator whose frequency is controlled by a crystal 43 as well as the usual compliment of program counter, instruction decode logic, register stacks and an ALU, all of these components being well-known and conventionally found in microprocessors. A variety of such microprocessors are available for use in implementations of the present invention.

The microprocessor 40 has an associated semiconductor ROM memory 42, a read/write or random access memory (RAM) 44, and a input/output interface 46 which are coupled to the microprocessor 40 via an address bus 48, a data bus 50 and a control bus 52. The ROM memory 42 typically contains a program of instructions while the RAM memory 44 will store programmable operands which may be telemetered into the implanted pacemaker 10 from an external programmer/monitor module (not shown) but which also is conventional in the art. In particular, the $A_s$ and $V_s$ inputs from the electrodes on the sensing/pacing leads 15 and 18 are applied to the microprocessor 40 via the I/O interface 46 and that interface is also used to couple the control signals $A_p$ and $V_p$ to the atrial pulse generator 14 (if used) and the ventricular pulse generator 26 at appropriate times as dictated by the program executed by the microprocessor 40.

Figure 3:
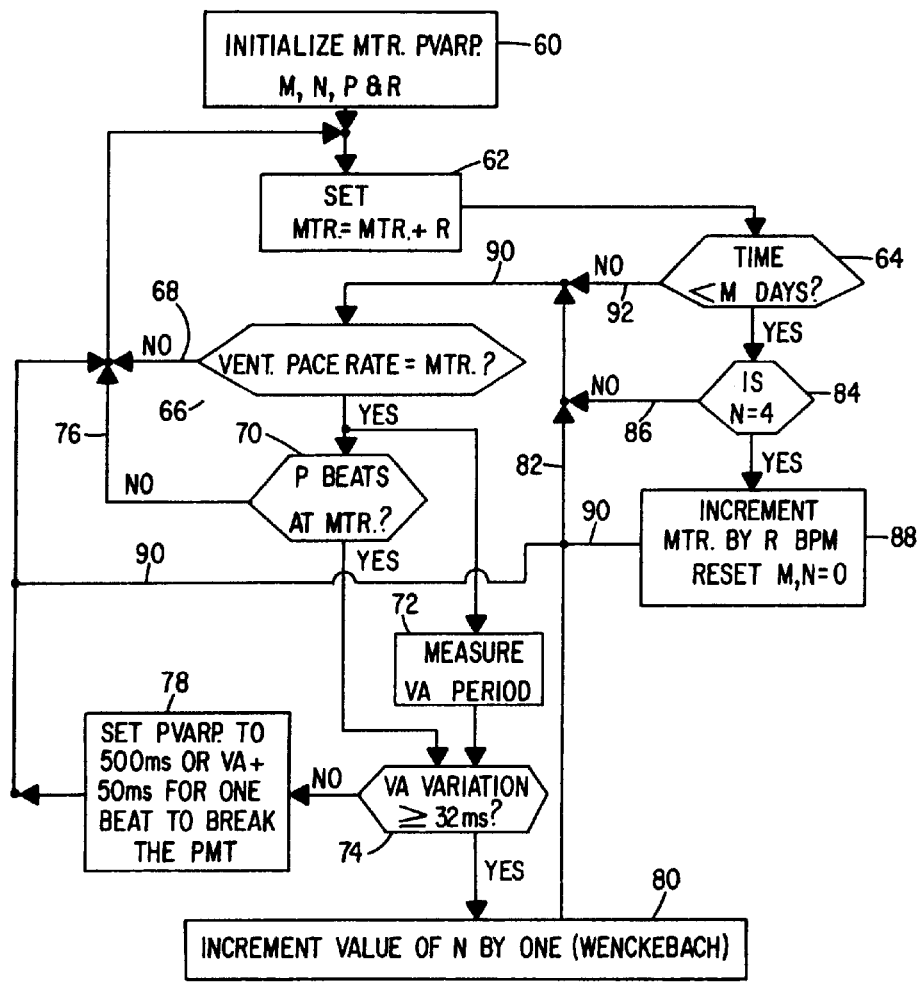
FIG. 3 is a schematic for diagram of a portion of the pacer control for atrial sensing and ventricular pacing showing one implementation of the invention.

FIG. 3 depicts a software flow diagram of one possible embodiment of a process or algorithm that can be implemented in the software executed by the microprocessor 40 of FIG. 2 in implementing a natural Wenckebach detection system with means to increment the MTR usable in either a rate-adaptive or non-rate-adaptive pacemaker. The process or algorithm begins at block 60 with the initialization or programming an initial value for MTR values for PVARP and certain constants M, N, P and R.

As will become apparent as the description of the invention continues, N is a natural Wenckebach count that is incremented by one for each natural Wenckebach episode. Episodes are accumulated for a predetermined value of M or until N=5. M, then, is the number of time units, typically measured in days, nominally a month or 30 days. P is a number of beats at MTR (e.g., 16 beats) and is also used in the determination and differentiation of Wenckebaching from PMT. MTR at block 60 is an initial programmed value of MTR selected by the user. R is a BPM increment to be added to MTR (e.g., 10 BPS).

Following the initialization steps, MTR is set equal to the programmed value of MTR plus the factor R at block 62. As test is then made at block 64 to determine whether M days have gone by since a preceding increment of MTR and, if not, control exits to decision block 66. By measuring the V—V interval between successive ventricular stimulating pulses, the ventricular pacing rate can be determined. The test at block 66 determines whether the ventricular pacing rate has risen to MTR and, if not, control returns, via path 68, whereby step 62 is again repeated.

When the test at decision block 66 reveals that the pacing rate has become equal to MTR, further tests are made at blocks 70, 72 and 74 with 72 being a time measurement to determine whether a predetermined number of successive ventricular beats, P, have taken place where the ventricular pacing rate has remained at MTR and whether the VA varies more than 32 ms between any beats. The value P is an arbitrary number, but a period of 16 beats has been determined to provide a sufficient sample. If the predetermined number of beats at MTR does not occur, control again returns via path 76 to the input of block 62.

When it is determined that the pacemaker is pacing the ventricle at MTR for the predetermined number of beats, it may be indicative that a PMT or natural Wenckebach is in progress and the algorithm provides for discriminating at 74. If the VA period varies less than 32 ms, this is indicative that a PMT is in progress and by increasing the PVARP to, say, 500 ms, or to a value based on the measured retrograde conduction time plus a constant time of, say, 50 ms at block 78, it is highly likely that the PMT will be broken since PVARP approaches the AA interval, and any retrograde conducted ventricular stimulating pulses would have taken place during the extended PVARP.

On the other hand, in accordance with the invention, if the VA period does vary by about 32 ms or more, the episode is determined to be a pacemaker Wenckebach situation at block 80 and a signal on lines 82 and 86 increments N at 86. When N=4 at 84 within a time period less than M days (possibly 30 days) at 64 this produces a control signal to be sent out from block along 90, 86 and 92 to cause an increment in MTR at 62 by R BPM and to reset M=0 and N=0 at 64 and 84, respectively. In this manner, the valve of MTR is adjusted upward based on 4 Wenckebach events occurring within M days. Of course, all the selected values, N, M, R, etc., are not meant to be limiting and are somewhat arbitrary examples which can be varied as indicated to better serve any particular situation.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A dual chamber cardiac pacemaker having an upper rate limit (URL) comprising:
    (a) sensor for sensing atrial depolarization events;
    (b) sensor for sensing ventricular depolarization events;
    (c) output device for stimulating a ventricular chamber;
    (d) first timer coupled to said sensor for sensing atrial depolarization events for determining a VA interval and establishing an AV interval between an occurrence of an atrial depolarization event and the time following such occurrence at which the output device for stimulating a ventricular chamber stimulates the ventricular chamber;
    (e) second timer coupled to said sensor for sensing ventricular depolarization events for sensing the VA interval;

(f) system for detecting the occurrence of pacemaker mediated tachycardia episodes from a predetermined interval at URL; and (g) distinguishing device for determining variations in the VA interval determined by said timers and for distinguishing Wenckebach episodes from pacemaker mediated tachycardia episodes based on said variations in VA intervals.

2. A dual chamber cardiac pacemaker as in claim 1 wherein the device for distinguishing Wenckebach episodes from pacemaker mediated tachycardia episodes comprises a device for comparing VA interval times for successive beats.

3. A dual chamber cardiac pacemaker as in claim 2 wherein the distinguishing device determines the existence of a Wenckebach episode when a beat to beat VA interval variation is between 5 ms and 50 ms.

4. A dual chamber cardiac pacemaker as in claim 2 wherein the distinguishing device determines the existence of a Wenckebach episode when a beat to beat VA interval variation $\geq 30$ ms.

5. A dual chamber cardiac pacemaker as in claim 1 including a device for counting Wenckebach episodes occurring within a predetermined time interval and further incrementing the pacemaker upper rate limit based on a predetermined Wenckebach episode frequency.

6. A dual chamber cardiac pacemaker as in claim 5 wherein the predetermined Wenckebach episode frequency is $\geq 3$ per month.

7. A dual chamber cardiac pacemaker as in claim 5 wherein said pacemaker upper rate limit is incremented by an amount in the range of 1–30 beats per minute.

8. A dual chamber cardiac pacemaker as in claim 1 including a device responsive to the distinguishing device for breaking the PMT episode, comprising a device for increasing a PVARP time interval for at least one beat to a predetermined value sufficient to insure that retrograde P-waves are not tracked by the device for stimulating a ventricular chamber.

9. A dual chamber cardiac pacemaker as in claim 8 wherein the predetermined value to which the PVARP time interval is increased for one beat is in the range of from 350 ms to 500 ms.

10. A dual chamber cardiac pacemaker as in claim 8 wherein the predetermined value to which the PVARP time interval is increased is a value equal to a measured time (VA) plus a constant time in the range of 5–100 ms.

11. A dual chamber programmable cardiac pacemaker having an upper rate limit comprising:

(a) means for sensing atrial depolarization events;

(b) means for sensing ventricular depolarization events;

(c) means for stimulating a ventricular chamber;

(d) first timing means coupled to the means for sensing atrial depolarization events for determining a VA interval and establishing an AV interval between the occurrence of an atrial depolarization event and the time following such occurrence at which the means for stimulating a ventricular chamber stimulates the ventricular chamber;

(e) second timing means coupled to the means for sensing ventricular depolarization events for sensing the VA interval and establishing a PVARP time interval during which the first timing means is inhibited from establishing an AV interval;

(f) means for detecting the occurrence of pacemaker mediated tachycardia episodes from a predetermined interval at URL; and (g) distinguishing means for determining variations in the VA interval determined by both said timer means and for distinguishing Wenckebach episodes from pacemaker mediated tachycardia episodes based on said variations in VA interval.

12. A dual chamber cardiac pacemaker as in claim 11 wherein the distinguishing means for distinguishing Wenckebach episodes from pacemaker mediated tachycardia episodes comprises a device for comparing VA interval times for successive beats.

13. A dual chamber cardiac pacemaker as in claim 12 wherein the distinguishing means determines the existence of a Wenckebach episode when a beat to beat VA interval variation is in the range between about 5 ms and 50 ms.

14. A dual chamber cardiac pacemaker as in claim 12 wherein the distinguishing means determines the existence of a Wenckebach episode when a beat to beat VA interval variation $\geq 30$ ms.

15. A dual chamber cardiac pacemaker as in claim 11 including a device for counting Wenckebach episodes occurring within a predetermined time interval and further incrementing the pacemaker upper rate limit based on a predetermined Wenckebach episode frequency.

16. A dual chamber cardiac pacemaker as in claim 15 wherein the predetermined Wenckebach episode frequency is $\geq 3$ per month.

17. A dual chamber cardiac pacemaker as in claim 15 wherein said pacemaker upper rate limit is incremented by an amount in the range of 1–30 beats per minute.

18. A dual chamber cardiac pacemaker as in claim 11 including means responsive to the detecting means for breaking the PMT episode comprising means for increasing a PVARP time interval for at least one beat to a predetermined value sufficient to insure that retrograde P-waves are not tracked by the means for stimulating a ventricular chamber.

19. A dual chamber cardiac pacemaker as in claim 18 wherein the predetermined value to which the PVARP time interval is increased for one beat is in the range of from 350 ms to 500 ms.

20. A dual chamber cardiac pacemaker as in claim 18 wherein the predetermined value to which the PVARP time interval is increased is a value equal to a measured time (VA) plus a constant time in the range of 5–100 ms.

* * * * *